United States Patent [19]
Wilson et al.

[11] Patent Number: 4,971,785
[45] Date of Patent: Nov. 20, 1990

[54] NON-ALCOHOLIC DELIVERY SYSTEM FOR ORALLY INGESTIBLE ACTIVE INGREDIENTS

[75] Inventors: Mark E. Wilson; B. Harrison Cole, both of Houston, Tex.

[73] Assignee: Spectrum Consumer Products Co., Inc., Houston, Tex.

[21] Appl. No.: 502,618

[22] Filed: Mar. 30, 1990

Related U.S. Application Data

[63] Continuation-in-part of Ser. No. 167,504, Mar. 14, 1988, Pat. No. 4,919,918.

[51] Int. Cl.$^5$ .......................... A61K 9/46; A61K 9/16
[52] U.S. Cl. ...................................... 424/44; 424/49; 426/650; 426/651
[58] Field of Search ................... 424/44, 49; 426/650, 426/651

[56] References Cited

U.S. PATENT DOCUMENTS

| | | | |
|---|---|---|---|
| 3,943,949 | 3/1976 | Ashton et al. | 132/321 |
| 3,976,601 | 8/1976 | Levin | 424/44 |
| 4,001,438 | 1/1977 | Marmo et al. | 424/49 |
| 4,033,365 | 7/1977 | Klepak et al. | 132/321 |
| 4,127,645 | 11/1978 | Witzel et al. | 424/44 |
| 4,311,720 | 1/1982 | Marmo et al. | 426/651 |
| 4,386,106 | 5/1983 | Merritt et al. | 426/650 |
| 4,414,990 | 11/1983 | Yost | 132/321 |
| 4,515,769 | 5/1985 | Merritt et al. | 424/49 |
| 4,568,560 | 2/1986 | Schobel | 424/49 |
| 4,610,890 | 9/1986 | Miller et al. | 426/651 |
| 4,689,235 | 8/1987 | Barnes et al. | 426/651 |
| 4,695,463 | 9/1987 | Yang et al. | 424/48 |
| 4,704,269 | 11/1987 | Kurab | 424/44 |
| 4,707,367 | 11/1987 | Miller | 426/651 |
| 4,803,082 | 2/1989 | Cherukuri et al. | 424/48 |
| 4,816,265 | 3/1989 | Cherukuri et al. | 426/548 |
| 4,919,918 | 4/1990 | Cole et al. | 424/44 |
| 4,931,293 | 6/1990 | Cherukuri et al. | 426/650 |

*Primary Examiner*—Shep K. Rose
*Attorney, Agent, or Firm*—Cooper & Dunham

[57] ABSTRACT

A non-alcoholic delivery system for active ingredients is disclosed which does not require the use of alcohol as a solvent. Surface acting agents, or surfactants, are used to reduce surface tension of the compound in solution, facilitating dissolution of all additives including non-soluble, spray-dried flavoring oils. Surface acting agents also may produce a foaming or effervescent effect, if desired. One formulation produces a good-tasting, desirable mouthwash with appropriate flavor concentrations, as well as other products.

17 Claims, No Drawings

NON-ALCOHOLIC DELIVERY SYSTEM FOR ORALLY INGESTIBLE ACTIVE INGREDIENTS

CROSS-REFERENCE

This application is a continuation-in-part of U.S. application Ser. No. 07/167,504 filed Mar. 14, 1988, now U.S. Pat. No. 4,919,918 the specification of which is hereby incorporated by reference into the present application.

BACKGROUND OF THE INVENTION

The present invention relates to a non-alcoholic, effervescent compound in wet or dry form for use as a delivery system for orally ingestible active ingredients, such as mouthwashes, cough and cold remedies, antipyretics, antacids, sleep aids and prescription and non-prescription drugs.

All individuals have varying minimum levels of bacteria found in their bodies. The sources of the different types of bacteria are diverse and, for example, may range from eating, to atmospheric and environmental conditions, to a simple contact with unspecified articles or one's hands and fingers. While the general types of bacteria are not ever likely to be completely eliminated, effective control of harmful bacterial growth is desired for good hygiene.

The principal growth stimuli for harmful oral bacteria are residual food and food sugars coupled with the natural moisture and temperature conditions of the mouth. Under such conditions, these stimuli provide for explosive growth of harmful bacteria. These oral bacteria secrete acidic residues which further exacerbate and increase instances of poor health, dental caries and periodontal disease.

Decaying food particles which become trapped between teeth or between teeth and gum areas also are inconvenient or difficult to remove and contribute to higher levels of acidity and poor health, dental caries and periodontal disease.

Compounds designed to clean the oral cavity and provide fresh breath are known. Generically, such compounds fall into two groupings: dentifrices and mouthwashes. Other compounds, generically described as breath mints or breath fresheners which may be delivered in gums, liquids, sprays or small tablet shapes, are not considered oral cavity cleaners.

Many orally ingestible preparations, such as mouthwashes, cold remedies, antipyretics, antacids, sleep aids and prescription and non-prescription drugs are supplied to users in solutions, some of which contain varying amounts of alcohol or solvents. Alcohol in such solutions has long been believed necessary as a solvent to dissolve the active ingredients and flavoring oils in such solutions. For example, alcohol is used as a solvent in mouthwashes, cough medicines and cold preparations in which decongestants, antihistamines, flavoring additives, and cough suppressants can be dissolved. Concentrations of flavoring oils in solution with alcohol often serve to mask the unpalatable taste of the active ingredients.

While the use of alcohol as a solvent enables the inclusion of various active ingredients and flavoring oils into a liquid, the inclusion of alcohol usually is not necessary for the effectiveness of the compound and can have many detrimental side effects upon the user of such compounds. Beyond presenting potential medical and health problems, its inclusion in orally ingested products also presents potential social implications for some users.

The medical implications of using alcohol in an orally ingested preparation are validated, for example, by explicit warning labels on mouthwashes and cough and cold preparations concerning the drowsiness which may result from ingesting the alcohol within the preparation, and recommendations to avoid operating heavy machinery and automobiles after ingesting the preparation. Also, individuals who can not afford to purchase liquor sometimes drink less expensive mouthwashes and cold and cough remedies to obtain the alcohol contained therein, risking the detrimental effects of ingesting a stimulant they do not need, as well as increasing their risk of overdosing on the stimulant.

Ingesting alcohol can have a range of from little impact up to and including death, depending upon the individual. If the individual is a toddler or a person over age 60, there is a distinct difference in metabolic absorption capabilities as compared to persons between these age categories. For example, many widely-sold mouthwashes, cough remedies and cold preparations carry label warnings against use by individuals age six and under. It is generally known that as a person ages past 60 his or her general ability to metabolize alcohol gradually diminishes until, by age 80, it reaches that of an approximately six year old child's metabolic absorption.

Additionally, alcohol and its abuses is a recognized major social problem. Abuse of alcohol in all its forms is considered an illness, and in some schools of thought, is believed to be passed genetically. Contact with nonbeverage alcohol can trigger setbacks in recovering alcoholics.

Accidental poisonings from ingesting alcohol-based products such as mouthwash and cold remedies have occurred. Further, accidental ingestion of alcohol-based products by diabetics may cause a dangerous insulin deficiency, as insulin is utilized by the body in digesting alcohol.

Economically, alcohol is the preferred solvent for many orally ingested additives. Solutions which contain alcohol taste better than those which do not, because alcohol acts as a solvent to dissolve flavoring oils. Further, together with masking the unpleasant tastes of active ingredients, relatively high concentrations of flavoring oils, such as peppermint or spearmint oil, are known to have an antimicrobial affect in a user's mouth and on teeth and gums, possibly descreasing the instance of tooth decay. An effective, orally ingestible delivery system for a broad range of active ingredients, prescriptive or non prescriptive, which contains high concentrations of flavoring oils and no alcohol, has been thought desirable but heretofore has not been available.

A large amount of all orally ingestible compounds, including mouthwashes, cold remedies and cough formulas, are packaged as liquids whose principal volume and weight comprises water. They are packaged in clear plastic containers without protective outer packaging, and are subject to product tampering, such as by "hair hypodermic" needles which can inject contaminants or poisons without being noticed by the consumer. Transportation of orally ingestible products in a dry form, and in single dosage, moistureproof packets enclosed in a general external consumer package or box, makes it more difficult to contaminate the product. Further, such compounds are much less expensive to transport in dry form than in liquid form. In many cases, the effectiveness of active ingredients is prolonged in a dry, rather than liquid, state.

Other orally ingestible compounds, particularly pain relievers and prescription drugs, are supplied in large tablet or capsule form, which some users find difficult to swallow, and which are difficult to administer to small children. These compounds often also have a known bitterness and are often difficult to administer to children, seniors, and other healthcare patients. The vast majority of pain relievers are available only in tablet form. It long has been desired to have a good tasting, water-soluble delivery of pain relievers to correct current difficulties and enhance indivicual compliance with recommended dosages.

Some vitamins also have a known bitterness and are difficult to administer to children as well as adults because of their traditional pill form of delivery. Vitamins which have been successful for children have been artificially colored or sweetened to mask the bitterness or may have been made chewable like candy to secure children's compliance with daily recommended dosage requirements. There are several liquid over-the-counter vitamin products which use comparable amounts of alcohol as a solvent as do many mouthwashes. The alcohol content ranges are from 5% to 20%. A water-soluble delivery system for vitamins thus is desirable.

Dry and tablet form orally ingestible compounds are known. For examples, U.S. Pat. Nos. 3,772,431 and 3,888,976 to Milkvy et al. disclose a dry tablet compound which, upon dissolution, provides a solution with desensitizing action to the teeth, effervescent cleaning action and gingival toning. Both patents disclose a basic mouthwash formulation, but do not address specific formulations or a delivery system for cold remedies, pain relievers, vitamins or prescription drugs. Milkvy et al also do not disclose the use of spray-dried flavoring oils.

Mouthwash tablets are disclosed in U.S. Pat. Nos. 3,577,490, 3,629,468, and 3,518,343. Each of the patents concerns a method for the manufacture of effervescent tablets which may be used for cleaning solid surfaces, including the teeth and gum areas of the oral cavity. For example, U.S. Pat. Nos. 3,518,343 and 3,577,490 to Welsh et al. address unsuccessful prior art effervescent tablets and the need for an effective tableting lubricant and water-soluble anti-microbial agent to improve manufacturing processes for water-soluble tablets containing antimicrobial agents. Welsh et al. do not address a delivery system for cold remedies, cough suppressants, vitamins, pain relievers and prescription drugs, but rather, disclose means to manufacture mouthwash tablets. U.S. Pat. No. 3,629,468 to Anderson also addresses inadequacies of prior methods of producing effervescent tablets and discloses a method of manufacture which eliminates heating and drying steps, increases storage life of the resulting product, and eliminates the need for inclusion, in the compounds, of inert fillers or buffers. In addition, Welsh et al and Anderson use a very small concentration of flavorings.

Cold preparations in effervescing tablet form also are known. However, because these tablets do not contain alcohol or another solvent, they do not contain high concentrations of flavoring oils and as a result have a weak or bitter taste.

It also is known to use flavorings in the form of spray-dried oils. See, for example, Cherukuri U.S. Pat. Nos. 4,753,805 and 4,803,082. However, those patents do not disclose the use of large concentrations of spray-dried flavorings as part of a delivery system for active ingredients. Other such patents are disclosed in the file history of applicants' above-mentioned patent application.

SUMMARY OF THE INVENTION

One object of the present invention is to provide an effervescent, non-alcoholic delivery system for active ingredients, which can be supplied in granulated, solid or tablet form.

Another object is to provide a delivery system which effectively dissolves active ingredients and contains a high concentration of flavoring agents to mask the bitter or otherwise unpleasant taste of the active ingredients.

Another object of the present invention is to provide a non-alcoholic delivery system with high concentrations of flavoring oils, which act as antimicrobial agents in the mouth.

The present invention is an improvement on the prior art, and discloses a good tasting, colorless or colored, effervescent, non-alcoholic delivery system which enables inclusion of high concentrations of active ingredients and flavoring oils while avoiding the harmful effects of alcohol, which is used as a solvent in many orally ingestible products. The inclusion of a high concentration of flavoring oils also permits otherwise unpleasant tasting medicines to be provided in an easy to swallow liquid, rather than large tablet or capsule form.

The present invention utilizes one or more of a group of surface acting agents, or surfactants, to act in place of a solvent, eliminating the need for alcohol or other solvents and enabling the use of relatively high concentrations of spray-dried flavoring oils.

DETAILED DESCRIPTION OF THE INVENTION

The present invention contemplates an effervescent, non-alcoholic delivery system for orally ingestible active ingredients, to be provided either pre-mixed with water, or in dry granular or tablet form. The dry mixture, when mixed with water, provides a colorless or colored liquid with concentrated flavoring which looks and tastes like popular, liquid, alcohol-containing preparations, but with none of the adverse side effects of alcohol-containing preparations.

A family of surface acting agents, or surfactants, enables the present invention to provide an effective, good tasting, colorless or colored, delivery system for active ingredients. Surfactants, when dissolved, concentrate near the surface of the solution, forming a layer between the solution and other additives. They reduce the surface tension between additives and water. Inclusion of a surfactant renders inclusion of alcohol unnecessary.

Surfactants which may be used for the purpose of the present invention include sodium laurylsulfate, sodium n-laurylsarcosinate, sodium alkylsulfoacetate, sulfocolaurate, sulfate monoglyceride and sodium monoglyceride. The surfactants may be ionic, non-ionic or anionic. However, othr surfactants known to those skilled in the art may be suitable for purposes of the present invention.

The invention involves the utilization of the family of surfactants to produce effective liquid and solid delivery systems for orally ingestible active ingredients. The surfactants act to disperse additives throughout the compound although the additives are not easily dissolved in water, including active ingredients and volatile flavoring oils used to create concentrated flavoring. The surfactants also act to maintain dispersion of the additives in water. Some surfactants create "foarming effects," while others do not. In a mouthwash, a foaming effect is desirable, while in an anti-pyretic, a non-foaming surfactant is used.

The ability of the surfactants to dissolve flavoring oils enables compounds to include high concentrations of such oils. In addition to improving the taste of orally ingested compounds, flavoring oils, such as spearmint oil and peppermit oil, display anti-microbial effects in the oral cavity, thereby reducing instances of tooth decay and bad breath, when the compound is a mouthwash. Other flavoring agents which are suitable for purposes of the present invention are thymol, menthol and methyl salicylate (wintergreen).

In a mouthwash, it has been found desirable to use essential oil flavorings in spray-dried form in amounts greater than about 20% by weight of the resultant compound. These spray-dried flavorings generally consist of favoring oils and/or oil soluble aromatic chemicals encapsulated in water-soluble gums or modified starches.

Effective amounts of one or more of the above-mentioned surfactants are added to the delivery system to insure dissolution of all ingredients when mixed with water. The surfactants will act to disperse the volatile oils uniformly throughout an aqueous solution when water is added, and to maintain dispersion.

If an effervescent liquid is desired, an effervescent couple may be included in the delivery system. The effervescent couple comprises at least one each of a pharmaceutically acceptable, solid organic or inorganic acid, and a solid base, such as any of the metal carbonate salts. The couple imparts a pleasant effervescence of the compound upon mixture with water, as the acid and base combine to produce carbon dioxide. The effervescing action also aids in mixing the other ingredients of the compound to achieve even dispersion and solubilization throughout the solution.

Prescription and non-prescription active ingredients and vitamins and minerals can be used in the delivery system. Examples of such active ingredients include:
dextromethorphan hydrobromide (cough suppressant)
chlorpheniramine maleate (antihistamine)
pseudoephedrine hydrochloride (decongestant)
acetaminophen (antipyretic)
pamabrom (diuretic)
phenylpropanolamine hydrochloride (appetite suppressant)
caffeine (stimulant)
guaifenesin (expectorant)
aluminum hydroxide (adsorbent)
aspirin (antipyretic)
diphenhydramine hydrochloride (sleep aid)
codeine (cough suppressant)
ibuprofen (antipyretic)

Other active ingredients also may be used within the delivery system of the invention.

A sweetening ingredient preferably is used in the formation. The sweetening ingredients may be sodium saccharin, aspartame, acesulfane-K or other suitable agent.

The compounds of the present invention can be mixed with water and bottled, or supplied dry in granular or table form. The dry mixture can be packaged in powdered form, for example, in unit dose, moisture proof packages. Traditional tablet lubricants may be added, and the mixture can be formed into tablets, through manufacturing techniques well known in the art. The tablets also may be packaged in individual moisture-proof packages.

The compounds also may be delivered via time-release mechanisms such as porous micro-sponge polymers, micropores, microspheres or microencapsulation methods. These time-release mechanisms entrap the dry particles and release them to provide precise and prolonged delivery. See, for example, Won U.S. Pat. No. 4,690,825. The non-alcoholic delivery system described herein is particularly suitable for use in connection with time-release mechanisms, as alcohol and other solvents may break down or dissolve such mechanisms, rendering them inoperative or ineffective.

If desired, water can be added to the dry mixture and the resulting solution can be bottled as a liquid. If an effervescent couple is included in the delivery system, the effervescent effect of the solid acid and solid base in solutoin will occur immediately upon addition of water to the dry mixture.

EXAMPLE ONE

Basic Formula

A presently preferred example of a basic formulation for use in the present invention comprises the following elements or compounds:
40–70% effervescent couple
0.5–10% sweetening ingredient
<1% surfactant
20–50% spray dried flavoring(s)

The above formulation uses more than 4.5 times the flavoring oils than other orally ingestible, non-alcoholic compounds, particularly mouthwashes, cough and cold preparations and some liquid vitamins. This significant increase in flavor concentration substantially improves the taste of the particular product and also displays anti-microbial activity on mouth, tooth and gum surfaces. Further, the flavoring oils and surfactants are believed to have anti-plaque effects. The present invention in dry form with its increased flavoring concentration can produce equal or greater flavoring concentration as those found in liquid, alcohol-based compounds.

The compound can be modified to include coloring agents and a variety of active ingredients. The sweetening ingredient and/or effervescent couple percentages then will be incrementally reduced to compensate for the presence of one or more of the modifying components.

Other examples of formulations useful in the invention are as follows:

EXAMPLE TWO

Mouthwash

55% effervescent couple
5% sweetening ingredient
2% surfactant
20% spray dried flavoring(s)
18% active ingredient(s)

EXAMPLE THREE

Vitamins and Minerals

| | Quantity | % by Weight |
|---|---|---|
| Active Ingredients: | | |

|                          | Quantity        | % by Weight |
|--------------------------|-----------------|-------------|
| Vitamins and minerals    | 1000 mg         | 33.3%       |
| Inactive Ingredients:    |                 |             |
| Surface acting agent     | 15 mg           | .5%         |
| Sweetening ingredient    | 180 mg          | 6%          |
| Spray dried essential oils | 605 mg        | 20.2%       |
| Effervescent couple      | 1200 mg         | 40%         |
| Total                    | 3000 mg (3 g)   | 100%        |

EXAMPLE FOUR

Anit-pyretic (Aspirin-based)

| Active Ingredients:      |                 |             |
|--------------------------|-----------------|-------------|
| Aspirin                  | 225 mg          | 18%         |
| Inactive Ingredients:    |                 |             |
| Surface acting agent     | 5 mg            | .4%         |
| Sweetening ingredient    | 95 mg           | 7.6%        |
| Spray dried essential oils | 400 mg        | 32%         |
| Effervescent couple      | 525 mg          | 42%         |
| Total                    | 1250 mg (1.25 g)| 100%        |

EXAMPLE FIVE

Anti-pyretic (Acetaminophen-based)

| Active Ingredients:      |                 |             |
|--------------------------|-----------------|-------------|
| Acetaminophen            | 225 mg          | 18%         |
| Inactive Ingredients:    |                 |             |
| Surface acting agent     | 5 mg            | .4%         |
| Sweetening ingredient    | 95 mg           | 7.6%        |
| Spray dried essential oils | 400 mg        | 32%         |
| Effervescent couple      | 525 mg          | 42%         |
| Total                    | 1250 mg (1.25 g)| 100%        |

EXAMPLE SIX

Anti-pyretic (Ibuprofen-based)

| Active Ingredients:      |                 |             |
|--------------------------|-----------------|-------------|
| Ibuprofen                | 200 mg          | 16%         |
| Inactive Ingredients:    |                 |             |
| Surface acting agent     | 5 mg            | .4%         |
| Sweetening ingredient    | 95 mg           | 7.6%        |
| Spray dried essential oils | 425 mg        | 34%         |
| Effervescent couple      | 523 mg          | 42%         |
| Total                    | 1250 mg (1.25 g)| 100%        |

EXAMPLE SEVEN

Cough and Cold Remedy (Children's Formula)

| Active Ingredients:         |                 |         |
|-----------------------------|-----------------|---------|
| Phenylpropanolamine hydrochloride | 9.4 mg    | .94%    |
| Chlorpheniramine maleate    | 1 mg            | .1%     |
| Acetaminophen               | 50 mg           | 5%      |
| Inactive Ingredients:       |                 |         |
| Surface acting agent        | 5 mg            | .5%     |
| Sweetening ingredient       | 25 mg           | 2.5%    |
| Spray dried essential oils  | 200 mg          | 20.0%   |
| Effervescent couple         | 678 mg          | 67.8%   |
| Hydroxypropyl methylcellulose | 31.6 mg       | 3.16%   |
| Total                       | 1000 mg (1 g)   | 100%    |

EXAMPLE EIGHT

Cough and Cold Remedy (Adult Formula)

| Active Ingredients:          |              |         |
|------------------------------|--------------|---------|
| Pseudoephedrine hydrochloride| 30 mg        | 3%      |
| Chlorpheniramine maleate     | 2 mg         | .2%     |
| Acetaminophen                | 225 mg       | 22.5%   |
| Dextromethorphan hydrobromide| 15 mg        | 1.5%    |
| Inactive Ingredients:        |              |         |
| Surface acting agent         | 5 mg         | .5%     |
| Sweetening ingredient        | 18 mg        | 1.8%    |
| Spray-dried essential oils   | 250 mg       | 25%     |
| Effervescent couple          | 400 mg       | 40%     |
| Hydroxypropyl methylcellulose| 55 mg        | 5.5%    |
| Total                        | 1000 mg (1 g)| 100%    |

In this formulation, for a night-time formula, a slightly greater amount of dyphenhydramine hydrochloride could be substituted for dextromethorphan hydrobromide, with hydroxypropyl methylcellulose then slightly reduced. Ibuprofen could also be substituted for acetaminophen, in a slightly lesser amount.

EXAMPLE NINE

Antacid

| Active Ingredients:        |               |         |
|----------------------------|---------------|---------|
| Aluminum hydroxide         | 300 mg        | 30%     |
| Calcium carbonate          | 110 mg        | 11%     |
| Inactive Ingredients:      |               |         |
| Surface acting agent       | 5 mg          | .5%     |
| Sweetening ingredient      | 17.5 mg       | 1.75%   |
| Spray-dried essential oils | 470 mg        | 47.0    |
| Citric acid                | 97.5 mg       | 9.75%   |
| Total                      | 1000 mg (1 g) | 100%    |

In this formulation, calcuim carbonate and citric acid form an effervescent couple.

EXAMPLE TEN

Antacid

| Active Ingredients:        |               |         |
|----------------------------|---------------|---------|
| Aluminum hydroxide         | 200 mg        | 20%     |
| Magnesium hydroxide        | 100 mg        | 10%     |
| Simethicone                | 25 mg         | 2.5%    |
| Calcium carbonate          | 200 mg        | 20%     |
| Inactive Ingredients:      |               |         |
| Surface acting agent       | 10 mg         | 1.0%    |
| Sweetening ingredient      | 20 mg         | 2.0%    |
| Spray dried essential oils | 395 mg        | 39.5%   |
| Citric acid                | 50 mg         | 5%      |
| Total                      | 1000 mg (1 g) | 100%    |

EXAMPLE ELEVEN

Appetite Suppressant

| Active Ingredients:              |               |         |
|----------------------------------|---------------|---------|
| Phenylpropanolamine hydrochloride| 75 mg         | 7.5%    |
| Caffeine                         | 100 mg        | 10.0%   |
| Inactive Ingredients:            |               |         |
| Surface acting agent             | 7.5 mg        | .75%    |
| Sweetening ingredient            | 10 mg         | 1.0%    |
| Spray dried essential oils       | 225 mg        | 22.5%   |
| Effervescent couple              | 582.5 mg      | 58.25%  |
| Total                            | 1000 mg (1 g) | 100%    |

EXAMPLE TWELVE

Night Time Sleep Aid

| Active Ingredients: | | |
|---|---|---|
| Dyphenhydramine hydrochloride | 25 mg | 2.5% |
| Acetaminophen | 200 mg | 20% |
| Inactive Ingredients: | | |
| Surface acting agent | 5 mg | .5% |
| Sweetening ingredient | 15 mg | 1.5% |
| Spray dried essential oils | 200 mg | 20% |
| Effervescent couple | 555 mg | 55.5% |
| Total | 1000 mg (1 g) | 100% |

It should be appreciated that although the invention has been described with reference to the best modes presently known to the applicants, other modes and uses will be apparent to those skilled in the art upon review of the specification. Practice of such other modes and uses will not depart from the spirit and scope of the invention.

We claim:

1. A dry, non-alcoholic delivery system for an additive or an active ingredient in tablet or in dry granular form adapted to be dissolved in water, comprising:
   (a) an effective amount of at least one active ingredient or additive consisting of an essential oil in a spray-dried form; and
   (b) an effective amount of one or more of the following surface acting agents selected from a group consisting essentially of sodium laurylsulfate, sodium n-laurylsarcosinate, sodium alkylsulfoacetate, sulfocolaurate, sulfated monoglyceride, and sodium monoglyceride, the surface acting agent acting in place of a solvent to reduce surface tension between the additive and active ingredient and the water, to disperse the additive and active ingredient and to render the use of alcohol as a solvent unnecessary.

2. A composition according to claim 1, further comprising at least one solid, pharmaceutically acceptable acid and at least one solid, pharmaceutically acceptable base, which are adapted to react to produce carbon dioxide when dissolved in water, causing effervescence.

3. A composition according to claim 1, further comprising an effective amount of ibuprophen as an active ingredient.

4. A composition according to claim 1, further comprising an effective amount of aspirin as an active ingredient.

5. A composition according to claim 1, further comprising an effective amount of codeine as an active ingredient.

6. A composition according to claim 1, further comprising a vitamin as an active ingredient.

7. A composition according to claim 1, further comprising a mineral as an active ingredient.

8. A composition according to claim 1, further comprising an effective amount of acetaminophen as an active ingredient.

9. A composition according to claim 1, further comprising an effective amount of an antacid as an active ingredient.

10. A composition according to claim 1, further comprising an effective amount of an appetite suppressant as an active ingredient.

11. A composition according to claim 1, further comprising an effective amount of a decongestant as an active ingredient.

12. A composition according to claim 1, further comprising an effective amount of a cough suppressant as an active ingredient.

13. A composition according to claim 1, wherein the additive comprises at least about 20% of a spray-dried essential flavoring.

14. A composition according to claim 1, wherein the active ingredient is delivered over a period of time.

15. A dry, non-alcoholic mouthwash compound in tablet or in dry granular form adapted to be dissolved in watr for cleaning and disinfecting an individual's mouth, teeth, gums and breath, comprising:
   (a) at least one solid, pharmaceutically acceptable acid and at least one solid, pharmaceutically acceptable base, which are adapted to react to produce carbon dioxide when dissolved in water causing effervescence and mixing action to evenly solubilize all active and inactive ingredients;
   (b) at least about 20% by weight of at least one additive consisting of an essential oil in spray-dried form;
   (c) an effective amount of one or more of the following surface acting agents selected from a group consisting essentially of sodium laurylsulfate, sodium n-laurylsarcosinate, sodium alkylsulfoacetate, sulfocolaurate, sulfate monoglyceride, and sodium monoglyceride, the surface acting agent acting as a solvent in water to reduce surface tension between the additive and the water, to disperse the additive, and to render the use of alcohol in the mouthwash unnecessary.

16. A method for cleaning the oral cavity, comprising placing an aqueous solution of an effervescing couple, a quatity of at least about 20% by weight of spray-dried volatile oil used as a flavoring agent, and one or more surface acting agents into the mouth and causing the surface acting agents to foam and disperse the flavoring agent by agitation of solution in the mouth.

17. A dry, non-alcoholic mouthwash compound adapted to be dissolved in water for cleaning and disinfecting an individual's mouth, gums and breath, comprising by weight about 20%–70% of an effervescent acid-base couple, less than about 10% of a sweetening ingredient, less than about 2% of a surface acting agent, and at least about 20% of a spray dried flavoring agent.

* * * * *